(12) United States Patent
Rehwald

(10) Patent No.: US 11,604,244 B2
(45) Date of Patent: Mar. 14, 2023

(54) T1-WEIGHTED TURBO-SPIN-ECHO MRI SEQUENCE FOR PRODUCING HIGH QUALITY DARK BLOOD IMAGES AT HIGH HEART RATES

(71) Applicant: Siemens Healthcare GmbH, Erlangen (DE)

(72) Inventor: Wolfgang G. Rehwald, Chapel Hill, NC (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/690,132

(22) Filed: Mar. 9, 2022

(65) Prior Publication Data

US 2022/0196774 A1   Jun. 23, 2022

Related U.S. Application Data

(63) Continuation of application No. 15/992,228, filed on May 30, 2018, now abandoned.

(51) Int. Cl.
*G01R 33/567* (2006.01)
*A61B 5/0245* (2006.01)
(Continued)

(52) U.S. Cl.
CPC ........ *G01R 33/5673* (2013.01); *A61B 5/0013* (2013.01); *A61B 5/0245* (2013.01);
(Continued)

(58) Field of Classification Search
None
See application file for complete search history.

(56) References Cited

U.S. PATENT DOCUMENTS 5,997,883 A     12/1999  Epstein et al.
2009/0005673 A1 *  1/2009  Rehwald ............ G01R 33/5601
                                                600/420
(Continued)

OTHER PUBLICATIONS

Taylor Chung, M.D. 2013 "What is it? Black Blood Imaging" Presentation at 2013 SPR Cardiac Session; 56 slides; Pub. Date 2013, https:/Avww.pedrad.org/Portals/5/Events/2013/Chung%20Cardiac.pdf (Year: 2013).*

(Continued)

*Primary Examiner* — Jason M Ip
*Assistant Examiner* — Renee C Langhals

(57) ABSTRACT

A T1-weighted turbo-spin-echo magnetic resonance imaging system configured to capture data associated with a subject's heart during a time period and produce MR images has a dark-blood preparation module, a data capture module, and an image reconstruction module. The dark-blood preparation module performs dark-blood preparation through double inversion during some, but not all of the heartbeats within the time period. The data capture module configured performs data readouts to capture imaging data of an imaging slice during every heartbeat in which dark-blood preparation is performed. The data capture module also performs a steady state maintenance step during every heartbeat in which dark-blood preparation is not performed in order to maintain maximum T1-weighting. The image reconstruction module configured to reconstruct a T1-weighted image based on the imaging data.

13 Claims, 12 Drawing Sheets

(51) Int. Cl.
    *A61B 5/00*     (2006.01)
    *G01R 33/56*     (2006.01)
    *A61B 5/1455*     (2006.01)
    *A61B 5/024*     (2006.01)
    *A61B 5/318*     (2021.01)

(52) U.S. Cl.
    CPC ...... *A61B 5/02416* (2013.01); *A61B 5/14551* (2013.01); *A61B 5/318* (2021.01); *A61B 5/7285* (2013.01); *G01R 33/5602* (2013.01)

(56) References Cited

U.S. PATENT DOCUMENTS

| | | | | |
|---|---|---|---|---|
| 2011/0133735 A1* | 6/2011 | Yokosawa | ............ | G01R 33/288 324/307 |
| 2012/0194187 A1* | 8/2012 | Rehwald | ............ | G01R 33/563 324/309 |
| 2017/0074959 A1* | 3/2017 | Li | ............ | G01R 33/5676 |
| 2018/0067184 A1 | 3/2018 | Weingartner et al. | | |
| 2018/0292489 A1* | 10/2018 | Zeng | ............ | G01R 33/5602 |

OTHER PUBLICATIONS

Spicher, N., Kukuk, M., Maderwald, S., & Ladd, M.E., Initial evaluation of prospective cardiac triggering using photoplethysmography signals recorded with a video camera compared to pulse oximetry and electrocardiography at 7T MRI, 2016, Biomedical engineering online, 15:126. (Year: 2016).*

Simonetti, O.P., Finn, J.P., White, R.D., Laub, G., & Henry, D.A., "Black blood" T2-weighted inversion-recovery MR imaging of the heart. Radiology, 1996, 199(1), 49-57. (Year: 1996).*

Edelman, Robert R., Daisy Chien, and Ducksoo Kim. "Fast selective black blood MR imaging." Radiology 181.3(1991): 655-660.

Boussel, Loic, et al. "Modified electrocardiograph-triggered black-blood turbo spin-echo technique to improve T1-weighting in contrast-enhanced MRI of atherosclerotic carotid arteries." Journal of Magnetic Resonance Imaging 28.2(2008): 533-537.

Simonetti O. P. et al; "Black blood T2-weighted inversion-recovery MR imaging of the heart"; Radiology; 1996;199(1); 49-57.

Finn J. P. et al; Cardiac MR Imaging: State of the Technology; Radiology; vol. 241; No. 2: pp. 338-354; 2006.

Ridgway J. P.; "Black Blood Versus Bright Blood Imaging"; 2015; Cardiovascular MR Manual; Springer; Cham. 97-104.

Foo Thomas K. F. et al; "Methods for Cardiac Magnetic Resonance Imaging"; Radiology Key; Dec. 26, 2015; radiologykey.com/methods-for-cardiac-magnetic-resonance-imaging/.

Spicher N. et al; "Initial evaluation of prospective cardiac triggering using photoplethysmography signals recorded with a video camera compared to pulse oximetry and electrocardiography at 7T MRI"; 2016; Biomedical engineering online; 15:126.

Taylor, Chung, M.D.: "What is it? Black Blood Imaging"; Presentation at 2013 SPR Cardiac Session; 56 slides; Pub.Date 2013, URL: https://www.pedrad.org/Portals/5/Events/2013/Chung%20Cardiac.pdf (Year: 2013).

Kim W. Y. et al; "Three-dimensional black-blood cardiac magnetic resonance coronary vessel wall imaging detects positive arterial remodeling in patients with nonsignificant coronary artery disease"; 2002 Circulation; 106(3); 296-299.

* cited by examiner

T1-WEIGHTED TURBO-SPIN-ECHO MRI SEQUENCE FOR PRODUCING HIGH QUALITY DARK BLOOD IMAGES AT HIGH HEART RATES

CROSS-REFERENCE TO RELATED APPLICATIONS

The present application is a continuation of U.S. patent application Ser. No. 15/992,228, titled T1-Weighted Turbo-Spin-Echo MRI Sequence for Producing High Quality Dark Blood Images at High Heart Rates, filed May 30, 2018, which is hereby incorporated by reference herein in its entirety.

TECHNICAL FIELD

The present invention relates generally to cardiovascular Magnetic Resonance Imaging (MRI), and, more particularly, to T1-weighted turbo-spin echo (TSE) imaging in a sequence which produces high quality dark blood images at high heart rates.

BACKGROUND

The dark-blood T1-weighted turbo-spin echo (TSE) sequence is a standard MRI pulse sequence that is commonly used for depicting cardiac and vascular morphology and for diagnosing cardiac tumors. In dark-blood imaging, pulses are timed to capture a null signal from flowing blood and thus represent the blood as a dark area in the image. Dark blood techniques are especially useful for visualizing intracavitary cardiac masses, which appear brighter than the dark blood pool in the cavity. The MM pulse sequence is synchronized to a physiological signal such as an electrocardiogram (ECG) or a pulse oximetry signal, and a portion of the image is read out (acquired) at each heartbeat by each echo train. In T1-weighted TSE (as opposed to T2-weighted TSE) the sequence is always arranged to readout at every heart beat (trigger pulse=1) resulting in the shortest possible effective time-to-repeat (TR) (equaling one RR-interval) to provide maximum T1-weighting.

Blood appears dark if its magnetization is zero at the time of the TSE data readout. Blood of non-zero magnetization is erroneously spatially encoded due to the flow- and motion-sensitivity of the TSE readout and can appear smeared across the entire image as a bright "haze." As a result, myocardium cannot be seen or its signal intensity is erroneously altered to disguise or misrepresent myocardial abnormalities. Intracavitary cardiac tumors can be missed due to this haze or due to the equal image intensity of a tumor and non-darkened blood.

Using conventional methods, TSE images depict blood sufficiently dark in subjects with low heart rates such that the contrast between blood and tissue is clear and the images can be relied upon for a diagnosis. Unfortunately, the capability of the dark-blood preparation to render blood magnetization zero is diminished with increasing heart rates, which are often found in cardiac subjects and naturally occur in children. In these subject groups, dark-blood performance of the standard T1-weighted TSE sequence is frequently so poor that image quality is insufficient to rely on for a diagnosis. Dark-blood performance is poor at higher heart rates using a T1-weighted TSE sequence because with the pulses occurring at every heartbeat, DB-prep occurs too often and blood magnetization recovers too quickly for the data capture to coincide with both the zero magnetization point and the heart being in diastole.

Dark-blood performance could be improved if the pulse sequence was synchronized not to every heartbeat, but to every other or every third heartbeat (trigger pulse=2 or 3). This would allow for a longer effective TR of two or three RR-intervals. Blood magnetization would then be about zero at the diastolic TSE readout in the dark-blood prepared heartbeats and would thus appear dark in the image, thereby avoiding artifacts. In other words, allowing for more time between dark-blood preparations allows the data readout to be timed to the zero-magnetization point of the blood. However, T1-weighted TSE cannot be adequately run with a trigger pulse of 2 or 3. Therefore, an alternative approach for improving dark-blood performance in T1-weighted TSE imaging at high heart rates is needed.

The present disclosure is directed to overcoming these and other problems of the prior art.

SUMMARY

Embodiments of the present invention address and overcome one or more of the above shortcomings and drawbacks, by providing methods, systems, and apparatuses related to a T1-weighted turbo-spin-echo MM sequence that produces high quality dark blood images at high heart rates.

In an exemplary embodiment, a computer-implemented method for performing a cardiovascular T1-weighted turbo-spin-echo magnetic resonance imaging sequence includes receiving a physiological signal from a subject, the physiological signal representative of the subject's heartbeat, and performing dark-blood preparation according to a trigger pulse of N, wherein the dark-blood preparation occurs only in every Nth heartbeat and N is greater than 1. The method also includes performing a data readout in every Nth heartbeat, wherein the data readout includes capturing imaging data associated with an imaging slice, and performing a steady-state maintenance step, wherein the steady-state maintenance steps are performed only for every heartbeat which does not include a data readout. The method further includes reconstructing a T1-weighted image of the imaging slice based on the imaging data received as a result of the data readouts.

In another exemplary embodiment, a computer-implemented method for producing a cardiovascular T1-weighted magnetic resonance image includes receiving a parameter representative of a subject's heartrate, determining a trigger pulse value N for an MM sequence based on the parameter representative of the subject's heartrate, and performing the MM sequence. The MRI sequence includes performing dark-blood preparation according to a trigger pulse of N, wherein the dark-blood preparation occurs only in every Nth heartbeat, and performing one of a data readout or a steady-state maintenance step for every heartbeat, wherein the data readout includes capturing imaging data associated with an imaging slice and both the data readout and the steady-state maintenance step saturate transverse and longitudinal magnetization of the tissue. The method further includes reconstructing a T1-weighted image of the imaging slice based on the imaging data received as a result of the data readouts.

In another exemplary embodiment, a T1-weighted turbo-spin-echo magnetic resonance imaging system configured to capture data associated with a subject's heart during a time period and produce MR images includes a dark-blood preparation module, a data capture module, and an image reconstruction module. The dark-blood preparation module is configured to perform dark-blood preparation through double inversion during some, but not all of the heartbeats within the time period. The data capture module is configured to perform data readouts to capture imaging data of an imaging slice during every heartbeat within the time period. The image reconstruction module is configured to reconstruct a T1-weighted image based on the imaging data. The image reconstruction module discards or ignores imaging data received from the data capture module which was captured during heartbeats in which the dark-blood preparation module did not perform dark-blood preparation.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The present disclosure describes a sequence for T1-weighted TSE MM which accounts for heart rate. According to various embodiments of the present invention, as described in further detail herein, the MM sequence utilizes an effective time-to-repeat (effective TR) needed for optimal dark-blood performance, while still executing each TSE readout at a trigger pulse of one. In some embodiments, a system identifies a trigger pulse which would place the data readout timing during an overlap of the null point of blood after dark-blood preparation and the heart being in diastole. This value depends on the heart rate of the subject at the time of imaging. The system then performs dark-blood preparation at the selected trigger pulse. During each heartbeat that contains such dark-blood preparation, a TSE readout is run to collect a portion of the data of one entire image. In the heartbeats without dark-blood preparation, a TSE readout is also run, but without collecting data which will be subsequently used in reconstructing the image. This TSE readout is a "dummy" readout which maintains the tissue magnetization in a steady state of maximum or near-maximum T1-weighting. In this way, the T1-weighting of the tissue is not affected by the higher trigger pulse. The resulting dark-blood performance is significantly improved over a conventional T1-weighted sequence using a trigger pulse of one at higher heart rates, producing high quality images which can be relied upon for subject diagnosis.

Figure 1A:
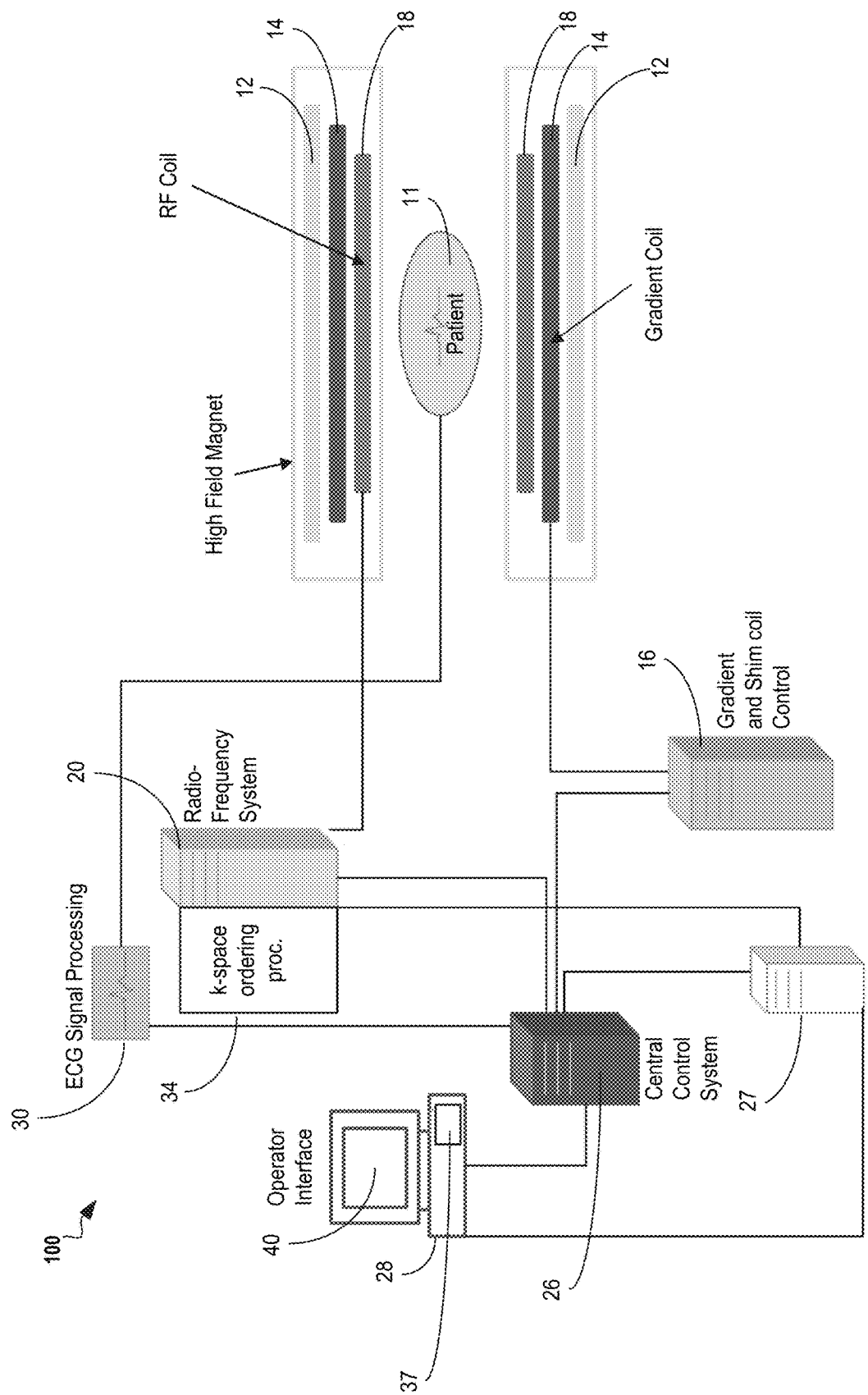
FIG. 1A is a schematic diagram of an exemplary MRI system, consistent with disclosed embodiments.

FIG. 1A shows an MRI system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field gradient pulses for magnetic resonance imaging pulse sequences. The shimmed gradients compensate for inhomogeneity and variability in an MRI device magnetic field resulting from patient anatomical variation and other sources. The magnetic field gradients include, for example, a dark-blood preparation magnetic field, a slice-selection gradient magnetic field, a phase-encoding gradient magnetic field, and a data readout gradient magnetic field that are applied to a selected anatomical area of interest of the patient 11.

A radio frequency (RF) module 20 provides RF pulse signals to RF coil 18, which in response produces magnetic field pulses which rotate the spins of the protons in the imaged body of the patient 11 by 90 degrees or by 180 degrees for so-called "spin echo" imaging, or by angles less than or equal to 90 degrees for so-called "gradient echo" imaging. Gradient and shim coil control module 16 in conjunction with RF module 20, as directed by central control system 26, control dark-blood preparation, data readout, slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space ordering processor unit 34 to provide a magnetic resonance dataset to an image data processor for processing into an image. In some embodiments, the image data processor is located in central control system 26. However, in other embodiments such as the one depicted in FIG. 1, the image data processor is located in a separate unit 27. Electrocardiogram (ECG) signal processing 30 provides ECG signals used for pulse sequence and imaging synchronization. A two or three dimensional k-space storage array of individual data elements in k-space ordering processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field and a sequence of gradient (coils 14) and RF (coil 18) pulses for use in acquiring multiple individual frequency components corresponding to individual data elements in the storage array. The individual frequency components are successively acquired, for example, using an imaging trajectory with a radial path as described in further detail below. A storage processor in the k-space ordering processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components which is substantially minimized.

Central control system 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control system 26 and enables user modification of magnetic resonance imaging signals in substantially real time. Continuing with reference to FIG. 1A, display processor 37 processes the magnetic resonance signals to reconstruct one or more images for presentation on display 40, for example. Various techniques known in the art may be used for reconstruction.

Figure 1B:
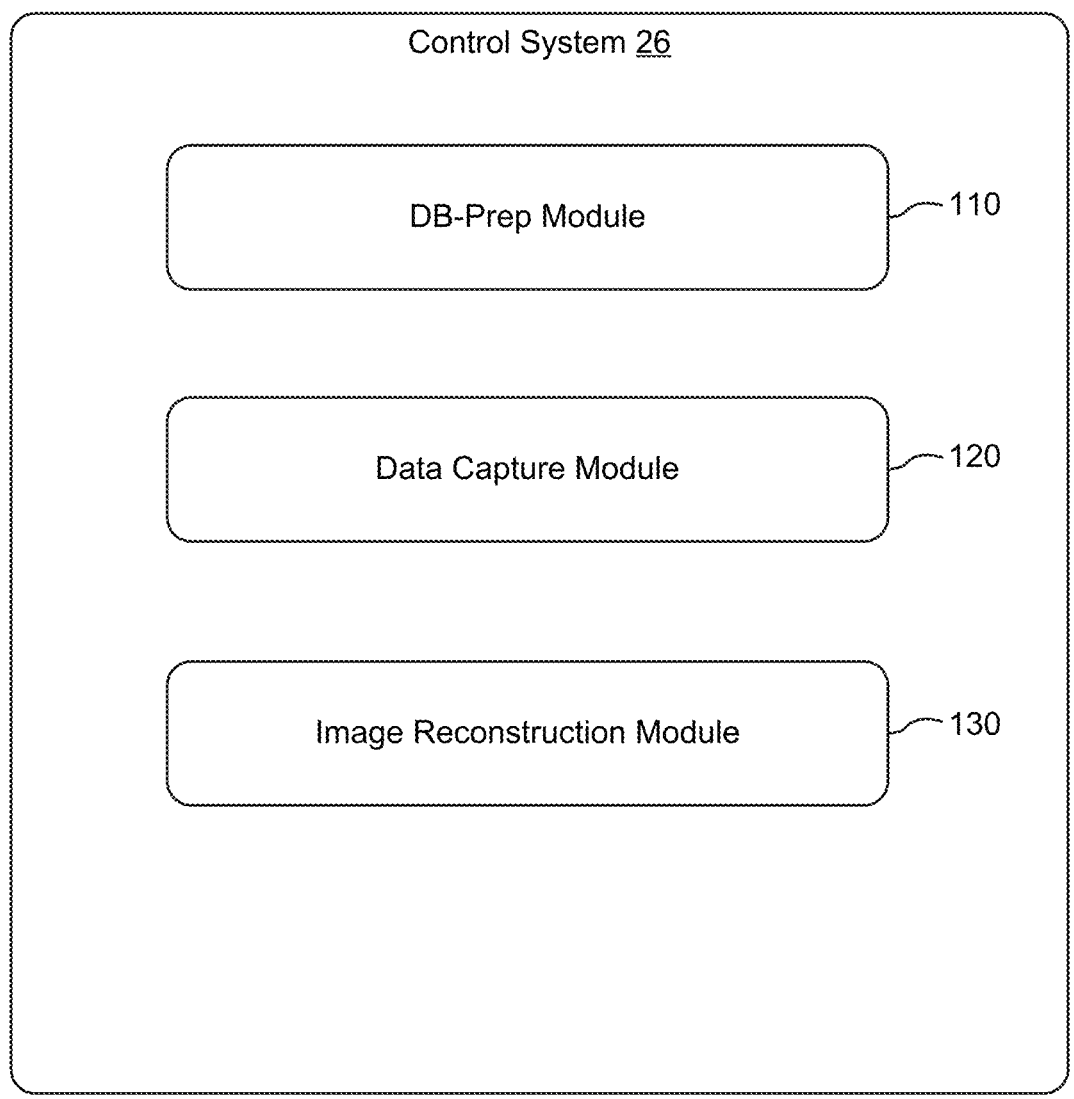
FIG. 1B is a schematic diagram of an exemplary control system for the MRI system of FIG. 1A, consistent with disclosed embodiments.

FIG. 1B is a schematic illustration of a plurality of modules which are provided in the MRI system 100. In the embodiment, of FIG. 1B, these modules are provided at the control system 26. However, it should be understood that these modules, which may be implemented in hardware and/or software, may be provided anywhere in MRI system 100. Moreover, each module may be configured to communicate with a particular component of the MRI system 100 in order to carry out a function, such as DB-prep, data readout, or image reconstruction. In an exemplary embodiment, the plurality of modules include a magnetic preparation module commonly known as a dark-blood preparation module (DB-prep module) 110, a data capture module 120, and an image reconstruction module 130. In order to produce images with dark-blood, the DB-prep module 110 is configured to send magnetization signals to prepare an area of a heart to be imaged. The data capture module 120 thereafter performs a data readout to capture data of a selected slice of the prepared area-based in part on the magnetization of the features (e.g., tissue, blood, etc.). The DB-prep module 110 sending signals and the data capture module 120 performing a data readout are paired steps which result in a snapshot of relevant data at a particular time. These paired steps are repeated several times to capture more and more data for the image. The image reconstruction module 130 translates the resulting data from different instances into an image of the heart in a manner known in the art.

In part to ensure that captured data includes the heart in the same or similar position at each data point, the paired steps are timed according to the cycles of the heart. The time needed by the heart to perform one full cardiac cycle is referred to as an "RR-interval" as it falls between two consecutive R-waves (peaks of an ECG wave). It is to be understood that the terms "cardiac cycle," "cycle," "heartbeat," and "RR-interval" are used interchangeably within the scope of this disclosure.

There are a number of parameters which must be set for MRI system 100 to perform an imaging sequence. These parameters include time-to-echo (TE), number of echoes per echo-train (also called turbo-factor (TF) or echo-train-length (ETL)), trigger pulse, and effective TR (which depends on the trigger pulse). MM system 100 can perform dark-blood TSE sequences according to parameter values selected based on the desired imaging results and characteristics. For example, different TSE MRI sequences can be configured for T1 or T2 image contrast (T1- or T2-weighting, respectively), depending on the selected parameters, as is known in the art.

Conventionally, a trigger pulse of one means that the paired sequence including both DB-prep and data readout is repeated every heartbeat. In other words, every heartbeat is a "use heartbeat" in which DB-prep and data readout occurs. A trigger pulse of two means that this sequence is executed every other heartbeat and the intermediate heartbeats are not used for imaging but for magnetization recovery. In this case "use heartbeats" and "recovery heartbeats" occur in an alternating manner. For a trigger pulse of three, two recovery heartbeats follow one use heartbeat.

The effective TR parameter, which is directly related to the quality of the contrast in the acquired image, is the amount of time between DB-prep being repeated. Since the paired sequence which includes DB-prep is timed to a particular point in the cardiac cycle, the effective TR parameter equals an integer multiple of the RR-interval (in seconds). The effective TR is thereby based on the trigger pulse. In particular, effective TR equals the RR-interval (in seconds) multiplied by the trigger pulse (e.g., trigger pulse of one means that effective TR equals one RR interval, trigger pulse of two means that effective TR equals two RR intervals, etc.).

In T2-weighting, an imaging sequence is run with a relatively longer effective TR (e.g., at least 1800 ms), which may require, for example, a trigger pulse of two (for an average RR-interval of approximately 900 ms). Higher heart rates with shorter RR-intervals may require a trigger pulse of three to ensure a sufficiently long effective TR. The relatively long effective TR minimizes the effect of T1 weighting. A long TE between 60 ms and 80 ms may be used to maximize T2 weighting. Together, the long TE and long effective TR result in as pure T2-weighting as possible in the confinement of a breath-hold.

For T1-weighting, the TSE sequence may be run with a trigger pulse of one in order to use the shortest possible effective TR (one RR-interval) to provide maximum T1 weighting. As described herein, a higher trigger pulse reduces the T1-weighting and therefore is not practical for a T1-weighted TSE sequence. A short TE in the range, for example, of 3-15 ms may be selected to impart T1-contrast. Also, the number of acquired echoes in the echo-train may be set to be relatively low (about 10-15 echoes, in one embodiment) to limit the ETL, as too long of an echo train would cause unwanted T2-weighting.

Figure 2:
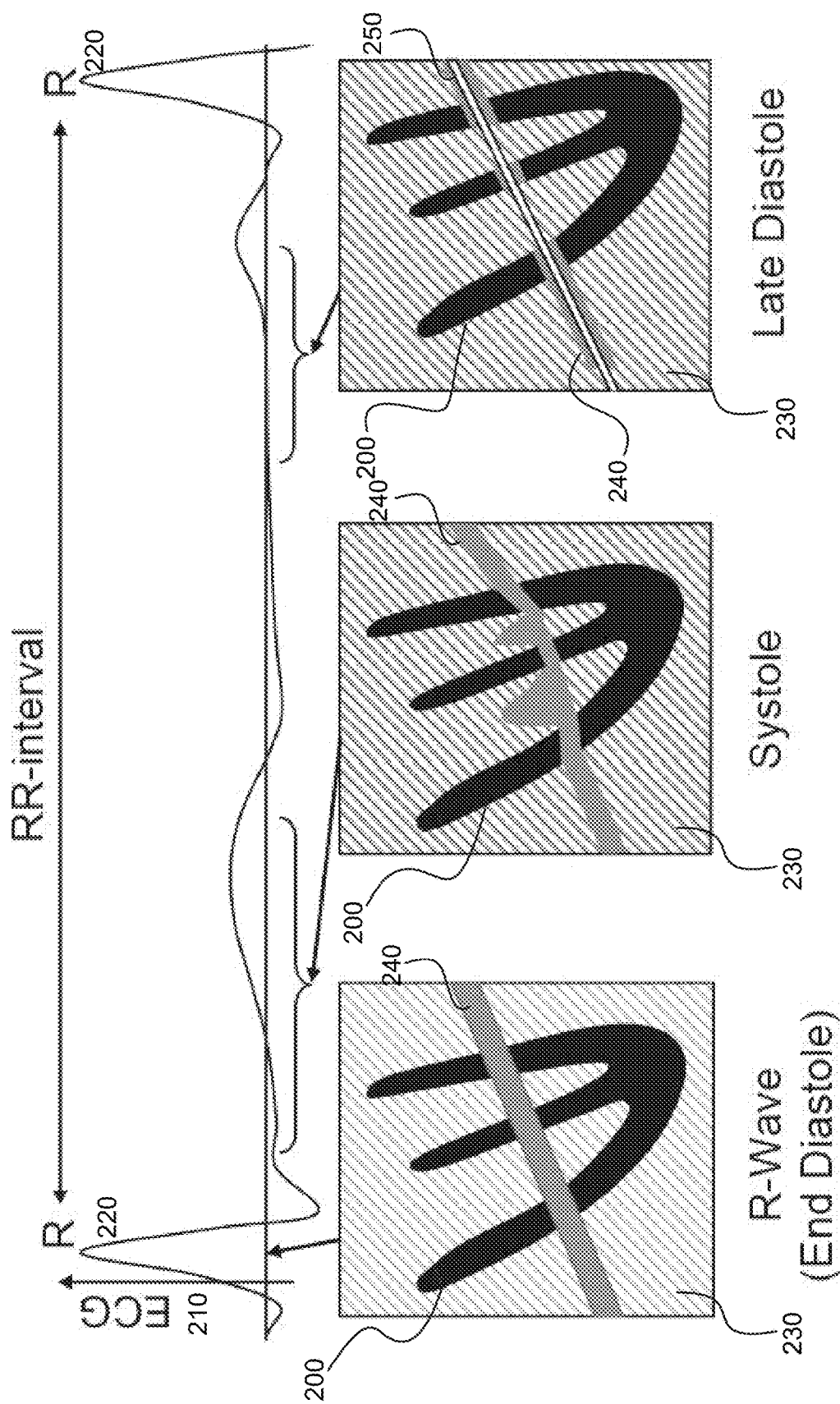
FIG. 2 is a diagram which illustrates some of the aspects of dark-blood preparation in cardiovascular MR imaging, specifically the optimal timing between dark-blood preparation at the R-wave and the data readout during diastole.

FIG. 2 is a diagram illustrating some features of a typical TSE MRI sequence, specifically its dark blood preparation. In an exemplary embodiment, a heart 200 is targeted for imaging. An example ECG wave 210 represents the cardiac cycle of the heart 200. The ECG wave 210 has a signal peak 220 known as the R-wave, indicating that the heart enters a new cardiac cycle. Cardiac contraction generally begins 50 ms-100 ms after the R-wave. The heart contracts and ejects blood (systole) before relaxing and refilling (diastole) and then restarting the cardiac cycle at the next R-wave.

The DB-prep module 110 is configured to apply magnetization pulses to an imaging volume 230. In an exemplary embodiment, the DB-prep occurs through double-inversion in which two 180° magnetization pulses are applied. The first 180° pulse is nonselective, inverting the magnetization for all slices within the imaging volume 230. The second 180° pulse, which immediately follows the first 180° pulse, is slice selective, returning the magnetization of only those features in a selected slab 240 back to the opposite direction. In this way, the myocardium and other stationary tissues within slab 240 have their signals preserved and slab 240 is called a "preservation slab;" but the blood outside slab 240 has an inverted magnetization. From the time of the application of the dark-blood preparation until the data readout in late diastole this blood from outside slab 240 flows into slab 240 while simultaneously undergoing magnetic recovery with time constant T1. The data capture module 120 performs a readout of an imaging slice 250 within the imaging slab 240 to capture data associated with the heart during the associated heartbeat.

The data readout performed by the data capture module 120 also has an effect on the tissue being imaged. In particular, the data readout step affects the T1-weighting of the heart tissue in imaging slice 250. If the data readout step is not performed during every heartbeat, the magnetization tends toward T2-weighting and maximum T1-weighting is not achieved. As a result, T1-weighted TSE is always run with a trigger pulse of one. While the described embodiment is for TSE sequences using turbo-spin echo trains for data readout, other embodiments may be applicable to other types of readouts. Examples of other data readouts that can be used for T1-weighted imaging include gradient-echo readouts and steady-state free precession readouts.

After DB-prep, the inverted magnetization of the inflowing blood recovers to the point of zero magnetization (before returning to non-inverted magnetization). Blood with zero or approximately zero magnetization is known as nulled blood or dark blood, as a data capture of the non-magnetized blood will produce a dark or black area in an MR image. The point of zero magnetization is referred to herein as the "dark-blood point."

Data readout should be timed to capture data at the dark blood point to optimize dark-blood performance. In order for this to occur, the data readout may be delayed until a systolic contraction to replace non-inverted blood in the preservation slab 240 with inverted blood from outside of the preservation slab 240. This requires the readout to take place during diastole, which may be about 600 ms to 850 ms after the DB-prep at the R-wave. This timing is also advantageous in that the motion-sensitive TSE readout falls into a diastolic phase which by definition possesses little motion.

Figure 3:
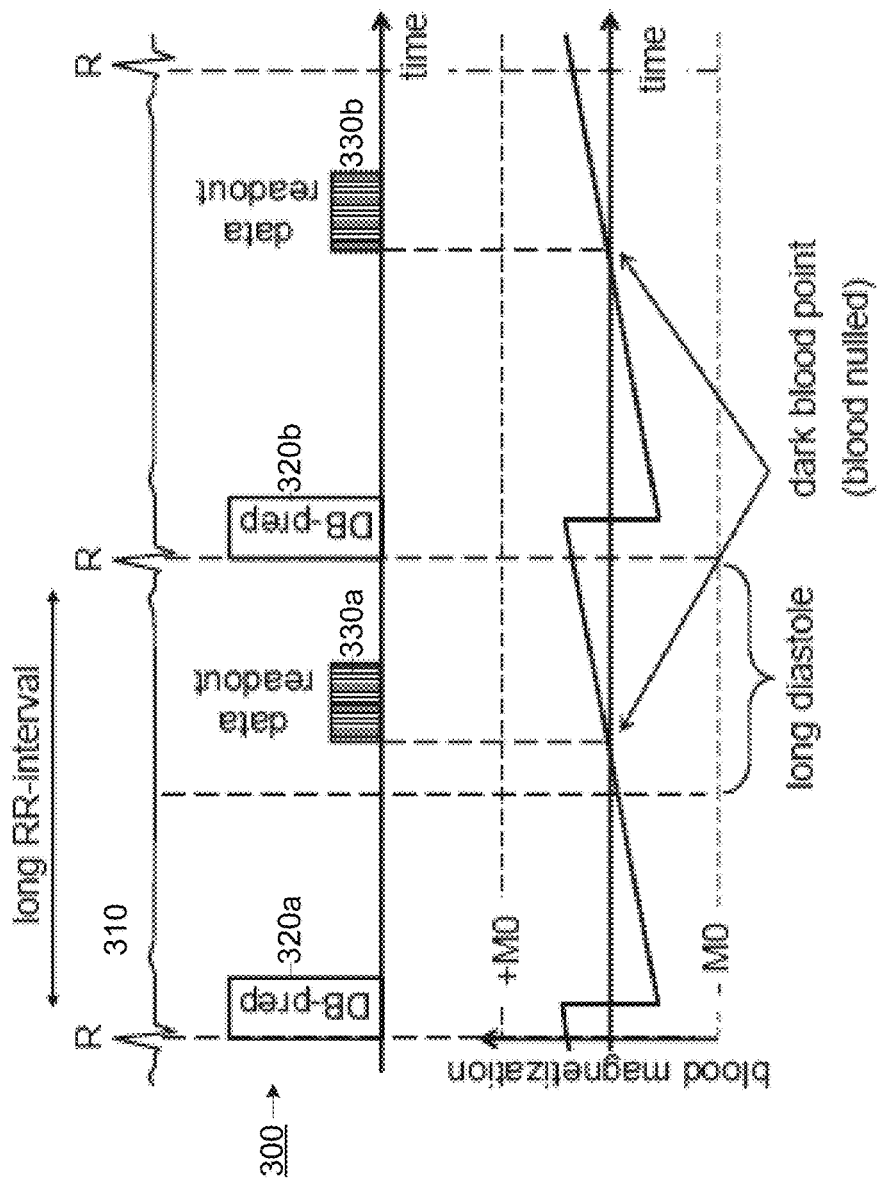
FIG. 3 is a diagram which graphically represents a conventional dark-blood prepared T1-weighted TSE MRI sequence with a low subject heart rate, and the resulting blood magnetization which crosses the zero-line at the beginning of the data readout.

FIG. 3 illustrates an example of a T1-weighted TSE pulse 300 sequence in which the subject has a relatively low heart rate (long RR-interval). The top line represents an ECG wave 310 for triggering each step of DB-prep 320a, 320b. Each DB-prep 320a, 320b immediately follows each R-wave of the ECG wave 310. A corresponding step of data readout 330a, 330b occurs after each DB-prep 320a, 320b, respectively, and is triggered based on a selected timing after the associated DB-prep 320a-b.

Each data readout 330a, 330b is preferably timed to occur at the dark blood point of the inflowing blood at diastole. The magnetization evolution of this inflowing blood is seen in the bottom diagram of FIG. 3. The magnetization of the blood is inverted by DB-prep 320a, 320b (but not re-inverted because it is not in the preservation slab 240 at the time of DB-prep 320a, 320b). The blood undergoes a recurring magnetization recovery after every inversion by the DB-prep 330a, 330b and is periodic with the RR-interval. The magnetization of tissue within the imaging slab is not shown but has maximum T1-weighting at the time of readout.

When a subject's heart rate is low (e.g., less than 80 beats per minute (bpm)), high-quality dark blood performance is expected, as each data readout 330a-b successively occurs at the dark blood point. The resulting images produced through TSE MRI can thus be expected to include clear demarcations between blood and tissue and should be able to be relied upon for diagnosis. However, while this effective timing can be achieved at low heart rates, higher heart rates do not allow for the same results.

Figure 4:
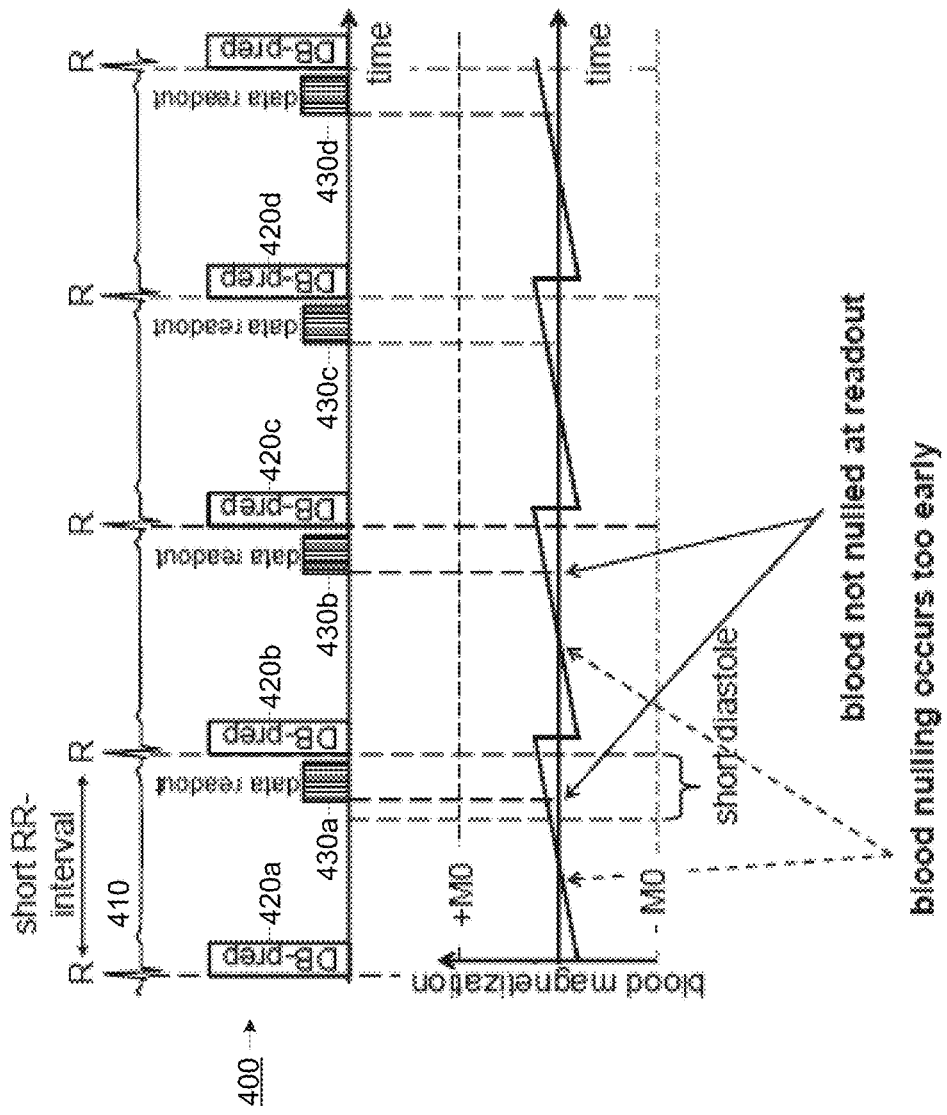
FIG. 4 is a diagram which graphically represents a conventional dark-blood prepared T1-weighted TSE MM sequence with a high subject heart rate, and the resulting blood magnetization which is not zero at the beginning of the data readout.

FIG. 4 illustrates an example of a T1-weighted TSE pulse sequence 400 in which the subject has a relatively high heart rate (short RR-interval). For example, 100 bpm (RR-interval of about 600 ms) is considered herein to be a "high" heartrate. The top line represents an ECG wave 410 for triggering each step of DB-prep 420a, 420b, 420c, 420d. As described herein, each DB-prep 420a, 420b, 420c, 420d immediately follows each R-wave of the ECG wave 410. Due to the high heart rate, the timing of corresponding data readouts 430a, 430b, 430c, 430d must be considered.

With a trigger pulse of one as mandatory for T1-weighting, the blood outside the preservation slab 240 sees so many inversion pulses per time period that it is significantly magnetically saturated. As a result, the magnetization of inflowing blood oscillates within a significantly smaller range compared to the lower heartrate case of FIG. 3. It follows that the inflowing blood recovers to zero magnetization (reaches the dark blood point) very early after the R-wave, for example at 300 ms. However, the data readout cannot occur at this point because the heart is still in systole. The systolic phase has so much cardiac motion that a TSE readout usually yields undiagnostic images. Further, the heart is in a different location during systole than at the R-wave (where it still has its diastolic position and shape), resulting in the preservation slab 240 and imaging slice 250 being misaligned, leading to a non-diagnostic image. For example, there may be partial regional inversion of the imaged slice, causing the data capture to misrepresent the underlying features.

As shown in FIG. 4, the data readouts 430*a*, 430*b*, 430*c*, 430*d* can be moved to the time period in which the heart is diastole. This generally overcomes the heart movement/slab misalignment problem, but at this time blood magnetization has partially recovered and has passed the dark blood point. This problem repeats at each data readout 430*a*, 430*b*, 430*c*, 430*d*. As a result, the captured data does not include blood at the dark blood point and instead includes non-zero blood magnetization. Non-zero blood magnetization causes severe artifacts when readout with TSE due to its flow sensitivity which causes incorrect spatial encoding. Blood appears "smeared" across such TSE images, which are frequently non-diagnostic and thus not reliable.

Figure 5A:
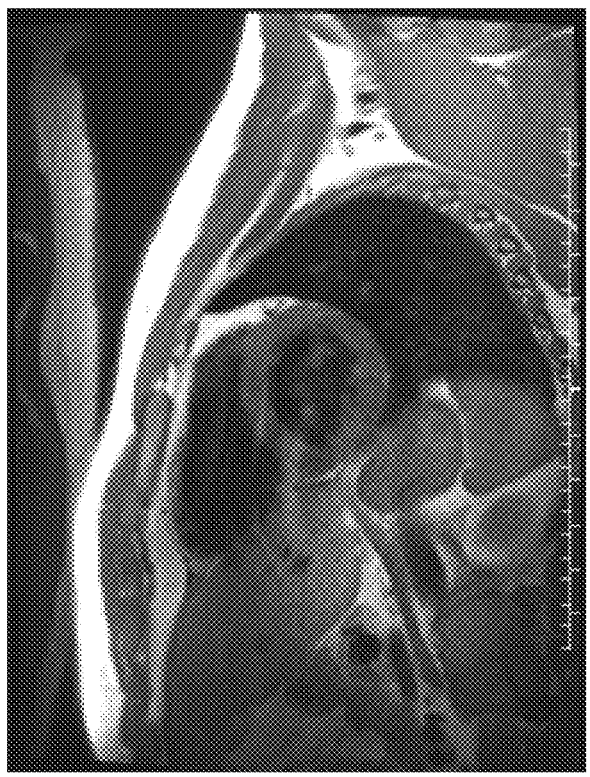
FIG. 5A is an MR image for a first slice location according to the conventional dark-blood prepared T1-weighted TSE MM sequence with high subject heart rate.
Figure 5B:
FIG. 5B is an MR image for a second slice location according to the conventional dark-blood prepared T1-weighted TSE MRI sequence with high subject heart rate.

FIGS. 5A and 5B show examples of two conventional dark-blood T1-weighted TSE images acquired in one subject at two slice locations. The subject of these images had a relatively high heart rate at the time of imaging (e.g., greater than 80 bpm). It can be clearly seen that the blood is not properly nulled, i.e., it is not completely black. Furthermore, there is a "haze" which overlays the heart, covering parts of the myocardium and thus reducing reliability of the image.

Therefore, because T1-weighted TSE requires a trigger pulse of one and a higher heart rates involve heartbeats which occur too quickly for the dark blood point to match up with the heart being in diastole during each heartbeat, a conventional dark-blood T1-weighted TSE sequence does not produce high quality, reliable images in high heart rate subjects. Moreover, image quality worsens with decreasing RR.

Presently disclosed embodiments of MRI system 100 are configured to perform a TSE sequence which includes a data readout (or a dummy-readout of the same magnetic saturation effect without using the readout data) during each heartbeat so that the tissue T1-weighting does not change from the conventional sequence, while executing the DB-prep only during certain heartbeats according to a trigger pulse determined by the subject's RR-interval. Conventionally, a trigger pulse of one in TSE MRI results in both DB-prep and data readout being performed every heartbeat. However, only the data readout step keeps the tissue magnetization in the imaged slice 250 in a steady state of maximum T1-weighting; the step of DB-prep does not create T1-weighting in the imaged slice 250. At least some disclosed embodiments thus "unpair" the DB-prep and data readout steps to allow DB-prep to be performed less often at high heart rates to avoid significant magnetic saturation of blood, while maintaining the maximum T1-weighting provided by the performance of the data readout with every heartbeat.

In order to provide the image reconstruction module 130 with the proper data for reconstructing an image, the data readouts which are performed during heartbeats that do not also include DB-prep are considered "dummy" readouts, as these readouts do not include usable data (due to the lack of a paired step of DB-prep). In other words, disclosed embodiments use only the readouts which are obtained during the heartbeats with a paired DB-prep for data acquisition. The purpose of the "dummy" readouts is to keep tissue magnetization in the maximum T1-weighted state. The "dummy" readouts are not used for image reconstruction. In some embodiments, any data collected is discarded or ignored. In other embodiments, no data is collected during these steps. In alternative embodiments, the "dummy" readout step is replaced with a similar step which achieves the goal of maintaining T1-weighting. For example, the MRI system 100 may be configured to perform slice-selective saturation preparation steps which have the same T1-weighting effect as a the dummy readout step, also without the capture of data. These steps which replace a conventional data readout step during certain heartbeats are generally referred to herein as steady-state maintenance steps.

Figure 6:
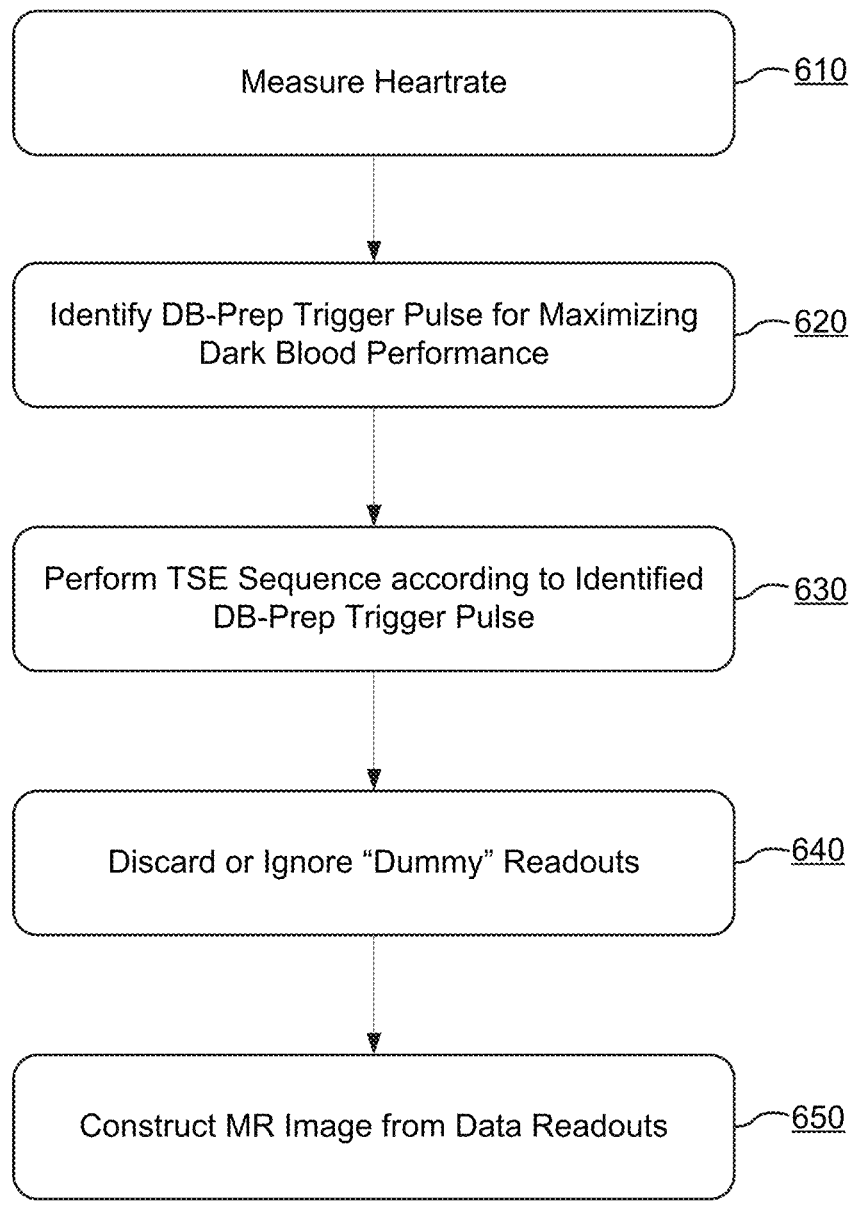
FIG. 6 is a flowchart of an exemplary dark-blood prepared T1-weighted TSE MRI sequence, consistent with disclosed embodiments.

FIG. 6 is a flowchart of an exemplary process 600 for producing T1-Weighted TSE MR images, according to a disclosed embodiment. In one embodiment, MRI system 100 is configured to perform one or more steps of the process 600. The MRI system 100 may include computing elements, such as a processor, memory, and I/O devices that are configured to carry out MM functions. The process 600 is performed in relation to a subject and is arranged to capture data and produce MR images of the subject's heart.

In step 610, the MRI system 100 measures the subject's heartrate. The MRI system may include a heartrate monitoring component or may be connected to one. Generally, the MM system 100 is executed during a breath-hold. The MRI system 100 may use an average heartrate during this time or may use a heartrate measurement prior to the breath-hold. The MM system 100 may be configured to obtain a heartrate in bpm or a measured RR-interval, or determine an RR-interval based on a measured bpm.

In step 620, the MRI system 100 identifies a DB-Prep trigger pulse for maximizing dark blood performance. The DB-prep trigger pulse is a parameter which identifies how often the DB-prep step will be performed during the imaging sequence. In particular, the MM system 100 determines a value N as the DB-prep trigger pulse which indicates that a DB-prep step will be performed only every Nth heartbeat. A DB-prep trigger pulse of two means that DB-prep is performed every other heartbeat, DB-prep trigger pulse of three means that DB-prep is performed every third heartbeat, and so on.

The MM system 100 determines the value N for the DB-prep trigger pulse based on a parameter representative of the subject's heartrate, such as a value for the subjects heartrate (in BMP) or the RR-interval. As described herein, higher heartrates are not compatible with a conventional trigger pulse (DB-prep and data readout) of one because DB-prep occurs too often and magnetically saturates the blood in the imaging area, causing blood nulling to occur too early in each cardiac cycle. The MRI system 100 is configured to determine a more appropriate trigger pulse which does not cause saturation and sufficiently delays the occurrence of the dark-blood point of the blood outside of the imaging slab such that the dark-blood point aligns with the heart being in diastole (instead of occurring sooner during systole). The MM system 100 is configured to calculate the DB-prep trigger pulse as function of the parameter representative of the subject's heartrate (e.g., bpm or RR-interval). In one example, the DB-prep module 110 compares the parameter representative of the subject's heartrate to one or more threshold values or uses a lookup tab to determine the DB-prep trigger pulse that best results in a data readout coinciding with the subject's heart being in diastole and is as close to one as possible.

In step 630, the MRI system 100 performs a T1-weighted TSE imaging sequence according to the identified DB-prep trigger pulse. In disclosed embodiments, the TSE imaging sequence uses the identified DB-prep trigger pulse (N) in that the DB-prep module 110 is triggered only in every Nth beat. As an example, a DB-prep trigger pulse of two means that every "use beat" (in which DB-prep is performed) is separated by a heartbeat in which no DB-prep is performed, referred to herein as a "blood recovery beat." The DB-prep module 110 is preferably triggered by a physiological signal, such as an ECG or pulse ox wave. For example, the DB-prep module 110 may be triggered every Nth R-wave.

The TSE imaging sequence also includes data readouts performed by the data capture module 120. In an exemplary embodiment, the data capture module 120 performs a data readout in every use beat. That is, for every heartbeat which includes DB-prep, a data readout is performed during that heartbeat. The data readout is timed to occur during diastole which is determined by the TSE imaging system 100 based on the heartrate (e.g., RR-interval).

In disclosed embodiments, the TSE imaging sequence further includes steady-state maintenance steps which occur during blood recovery beats. The steady-state maintenance step may be a magnetic saturation pulse and take the place of the data readout step during blood recovery beats. The steady-state maintenance step maintains the magnetic saturation of the tissue within the imaging slice 250 in the same or similar manner as a data readout step. In an exemplary embodiment, the steady-state maintenance step is a "dummy" readout in which the data capture module 120 performs a data readout, but data is not ultimately used in image reconstruction.

In step 640, the MRI system 100 discards or ignores the "dummy" readout. In one example, the data capture module 120 deletes or overwrites the data associated with "dummy" readouts and does not transmit anything to the image reconstruction module 130. In other embodiments, the data capture module 120 delivers data associated with "dummy" readouts to the image reconstruction module 130. The image reconstruction module 130 determines that the data is associated with a "dummy" readout and discards, ignores, or otherwise deletes the data. For example, the image reconstruction module 130 may use the DB-trigger pulse to determine which received data sets are associated with use beats and which data sets are associated with blood recovery beats. The image reconstruction module 130 may subsequently utilize the data sets associated with use beats and discard, ignore, or otherwise delete data sets associated with blood recovery beats.

In step 650, the MRI system 100 reconstructs an MR image using the received data. The image reconstruction module 130 uses data captured by the data capture module 120 to produce an MR image. The MR image is preferably in the same form and format as a conventional MR image, including image slices of the subject's heart. As described herein, the image reconstruction module 130 uses only data sets which are captured during use beats and either discards or never receives data sets associated with blood recovery beats. The resulting MR image is T1-weighted due to the one of the combination of data readouts and steady-state maintenance steps occurring during each heartbeat during the sequence.

Figure 7:
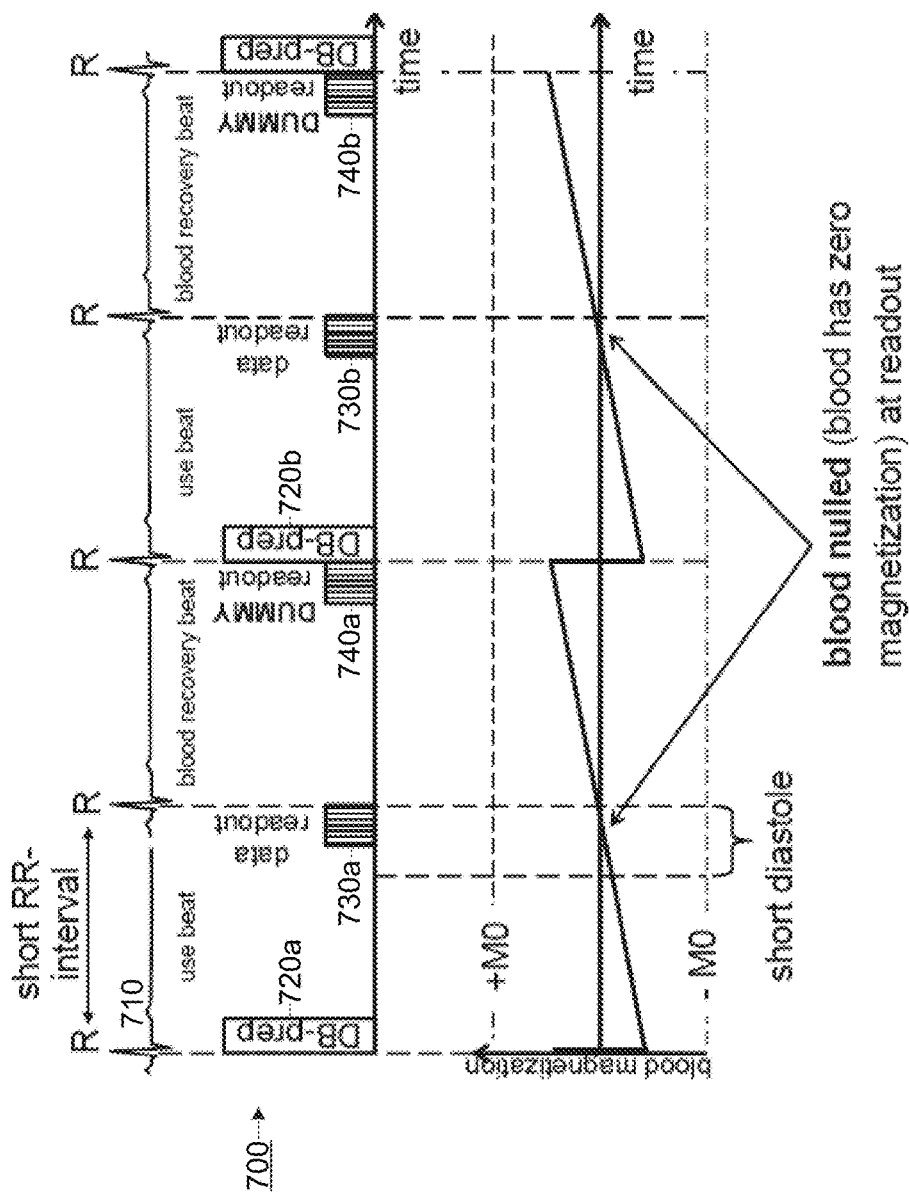
FIG. 7 is a diagram which graphically represents an exemplary dark-blood prepared T1-weighted TSE MRI sequence having a DB-prep trigger pulse of greater than one, consistent with disclosed embodiments.

FIG. 7 shows a T1-weighted TSE sequence 700 with DB-prep trigger pulse of two, according to an exemplary embodiment. The top line represents an ECG wave 710 for triggering each step of DB-prep 720a, 720b. The TSE sequence further includes data readout steps 730a, 730b and steady-state maintenance steps 740a, 740b. The blood flowing into the imaging slab magnetically recovers over the course of two heartbeats. This is due in part to the spacing of the steps of DB-prep 720a, 720b, which inhibits magnetic saturation of the blood which would cause magnetic recovery to occur too early in the cardiac cycle. As a result, the dark blood point occurs later and overlaps with a time period in which the subject's heart is in diastole, providing consistency to the image slices and reducing the chance of artifacts and blurring or hazing of the image. Moreover, the subject's heart tissue in the imaging slab receives a data readout 730a, 730b or a steady-state maintenance step 740a, 740b at every heartbeat, thereby mimicking a conventional trigger pulse of one and maximizing T1-weighting of the image.

In the embodiment of FIG. 7, the steady-state maintenance steps 740a, 740b are "dummy" readouts in which the data capture module 120 performs a data readout similar to the data readouts 730a, 730b. The "dummy" readouts include a data capture, however the data is not used for image reconstruction.

Figure 8:
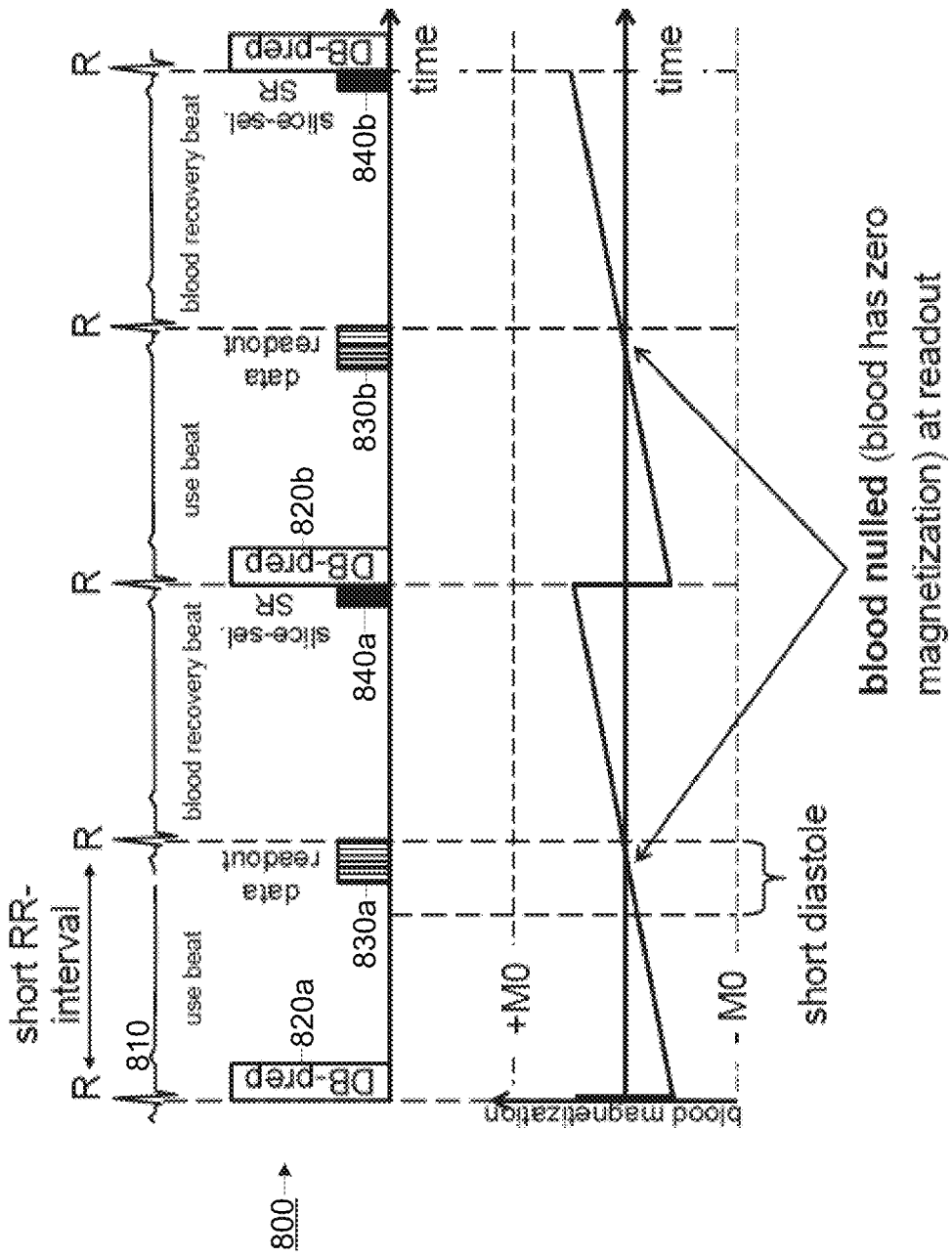
FIG. 8 is a diagram which graphically represents another exemplary dark-blood prepared T1-weighted MRI sequence having a DB-prep trigger pulse of greater than one wherein slice-selective saturations are performed.

FIG. 8 shows another embodiment of an exemplary TSE MRI sequence 800 with respect to an ECG wave 810. The sequence 800 is similar to the sequence 700, including DB-prep 820a, 820b according to a DB-prep trigger pulse of two, data readouts 830a, 830b during use beats and steady-state maintenance steps 840a, 840b during blood recovery beats. However, in sequence 800, the steady-state maintenance steps 840a, 840b are slice-selective saturation preparation pulses instead of "dummy" readouts. The data capture module 120 (or another component of MRI system 100, such as DB-prep module 110 or another prep module not shown) is configured to apply a magnetic pulse which mimics that of the data readouts 830a, 830b in that it produces a slice-selective pulse which saturates transverse and longitudinal magnetization of the tissue. The slice-selective saturation preparation has substantially the same effect as a data readout, because a readout of typical length (50 ms to 150 ms) also saturates transverse and longitudinal magnetization in the imaging slab. The slice-selective saturation preparation has the same magnetic saturation effect as a data readout, but does not capture any data, which advantageously requires lower energy and power.

Figure 9:
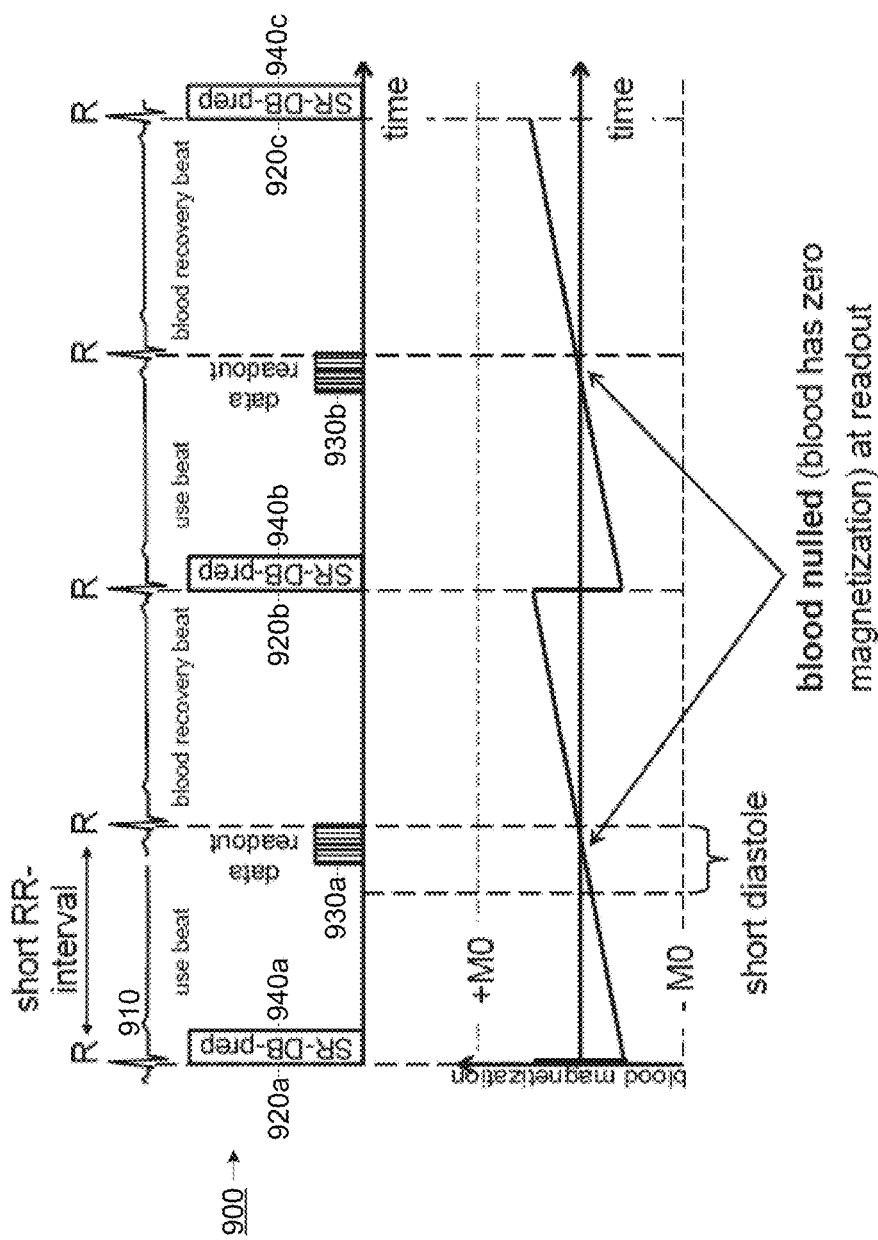
FIG. 9 is a diagram which graphically represents yet another exemplary dark-blood prepared T1-weighted MRI sequence having a DB-prep trigger pulse of greater than one wherein a slice-selective saturation is performed in the DB-module.

FIG. 9 shows yet another embodiment of an exemplary TSE MRI sequence 900 with respect to an ECG wave 910. The sequence 900 is similar to the sequences 700 and 800, including DB-prep 920a, 920b, 920c according to a DB-prep trigger pulse of two and data readouts 930a, 930b during use beats, and steady-state maintenance steps 940a, 940b, 940c. In sequence 900, however, the steady-state maintenance steps 940a, 940b, 940c are slice—selective saturations and are integrated into the DB-prep 920a, 920b, 920c. For example, the slice-selective saturation preparation described with respect to FIG. 8 may be combined with the steps of DB-prep 920a, 920b, 920c. In this modified DB-prep (SR-DB prep), the slice-selective inversion preparation commonly used in standard DB-prep is replaced by a slice-selective saturation recovery (SR) preparation. In one embodiment, the slice-selective inversion pulse of each step of DB-prep is replaced by a slice-selective saturation pulse. In one embodiment, a spoiler gradient pulse is performed as part of the SR-DB prep, in addition to the non-selective inversion pulse and slice-selective saturation pulse. The spoiler gradient pulse may be performed after the two other pulses of DB-Prep.

The integrated combination is in part possible because the steady-state maintenance steps of the disclosed embodiments occur close enough in time to the steps of DB-prep such that moving the timing of the saturation preparation to occur with the DB-prep of the next heartbeat does not significantly impact image contrast. This embodiment has the advantage that the tissue magnetization during data readouts 930a, 930b are independent of the duration of the previous RR-interval, as the magnetization in the prepared slab is reset with the saturation in the SR-DB-prep and is read out at exactly the same time after each SR-DB-prep 920a, 920b, 920c. Signal oscillations due to the natural variation of the RR-interval during the acquisition of one image and concomitant ghosting artifacts are thus avoided.

The disclosed embodiments include TSE MRI sequences which are designed to maintain maximum T1-weighting by including data readouts or a similar steady-state maintenance step with every heartbeat while also timing the data readouts which are used in image reconstruction to instances in which the dark blood point occurs during diastole. The MRI system 100 is configured to perform a T1-weighted TSE sequence according to disclosed embodiments in order to produce an MR image with high quality dark blood performance. The disclosed sequences are particularly applicable to instances in which the subject has a high heart rate (e.g., greater than 80 bpm), but could be applied in other situations depending on the desired characteristics of the MM.

Figure 10A:
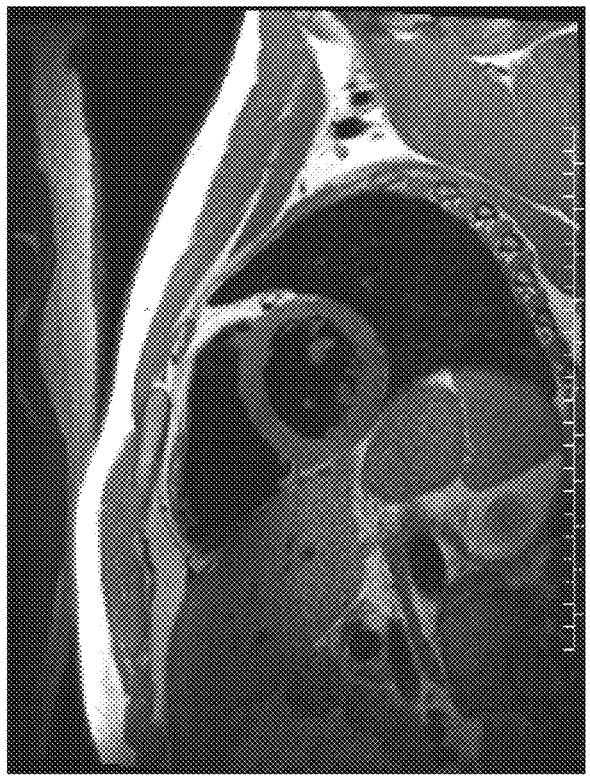
FIG. 10A is an MR image produced for a first slice location according to a disclosed T1-weighted MM sequence having a DB-prep trigger pulse of greater than one with high subject heart rate.
Figure 10B:
FIG. 10B is an MR image produced for a second slice location according to a disclosed T1-weighted MM sequence having a DB-prep trigger pulse of greater than one with high subject heart rate.

FIGS. 10A and 10B show T1-weighted TSE images acquired by a MRI system using a sequence consistent with those described herein, such as those shown in FIGS. 7-9. The images were acquired in the same subject at the same two slice locations as those in FIGS. 5A-5B. The MM system 100 used parameters which follow a conventional T1-weighted TSE sequence except for that a DB-trigger pulse of greater than one was used and "dummy" readouts were used during blood recovery beats. A comparison to the images of FIGS. 5A-5B shows a clear improvement of dark blood performance and depiction of the myocardium.

Figure 11:
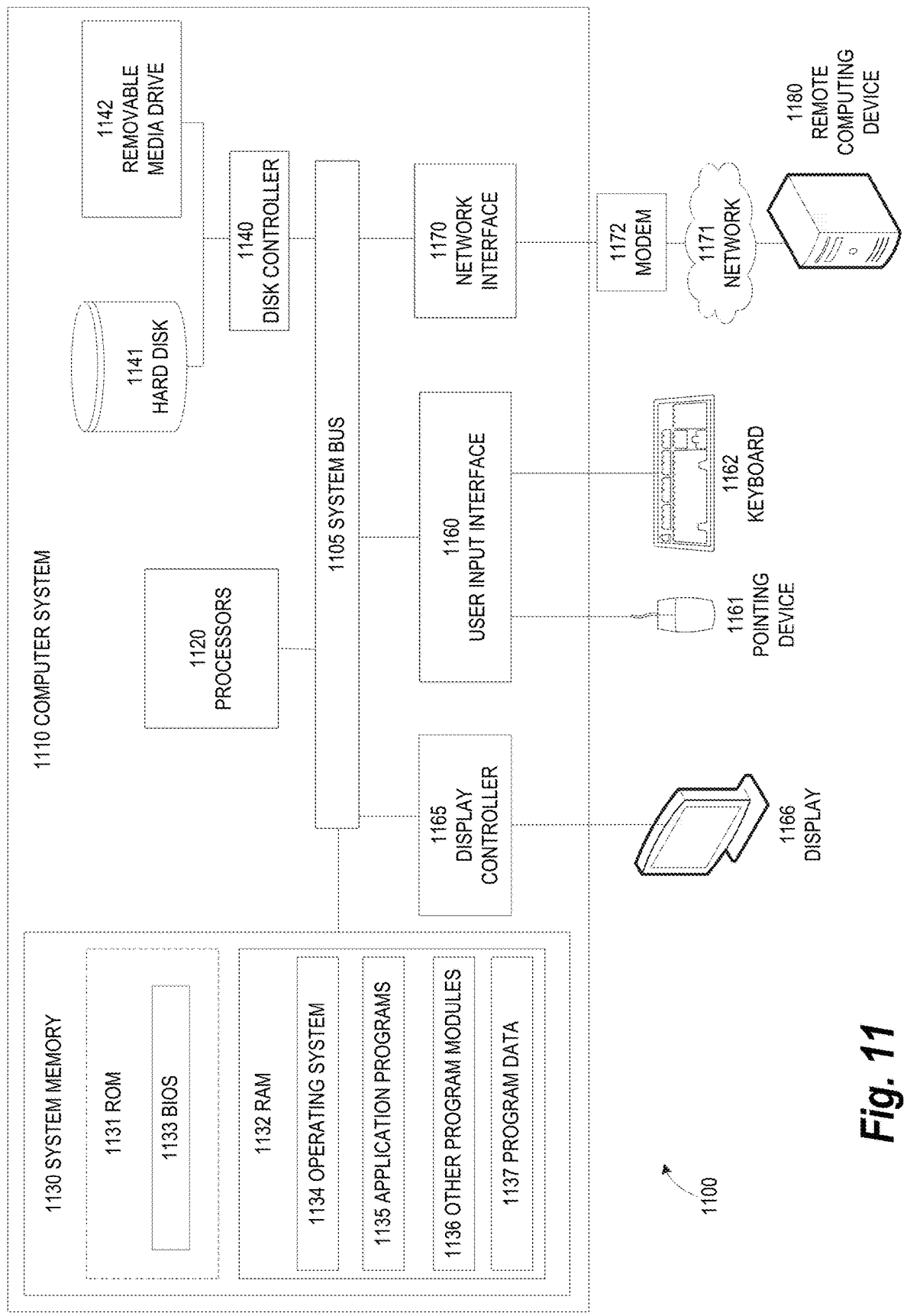
FIG. 11 illustrates an exemplary computing environment within which embodiments of the invention may be implemented.

FIG. 11 illustrates an exemplary computing environment 1100 within which embodiments of the invention may be implemented. For example, this computing environment 1100 may be configured to execute an imaging process performed by the MRI system 100. The computing environment 1100 may include computer system 1110, which is one example of a computing system upon which embodiments of the invention may be implemented. Computers and computing environments, such as computer system 1110 and computing environment 1100, are known to those of skill in the art and thus are described briefly here.

As shown in FIG. 11, the computer system 1110 may include a communication mechanism such as a bus 1105 or other communication mechanism for communicating information within the computer system 1110. The computer system 1110 further includes one or more processors 1120 coupled with the bus 1105 for processing the information. The processors 1120 may include one or more central processing units (CPUs), graphical processing units (GPUs), or any other processor known in the art.

The computer system 1110 also includes a system memory 1130 coupled to the bus 1105 for storing information and instructions to be executed by processors 1120. The system memory 1130 may include computer readable storage media in the form of volatile and/or nonvolatile memory, such as read only memory (ROM) 1131 and/or random access memory (RAM) 1132. The system memory RAM 1132 may include other dynamic storage device(s) (e.g., dynamic RAM, static RAM, and synchronous DRAM). The system memory ROM 1131 may include other static storage device(s) (e.g., programmable ROM, erasable PROM, and electrically erasable PROM). In addition, the system memory 1130 may be used for storing temporary variables or other intermediate information during the execution of instructions by the processors 1120. A basic input/output system (BIOS) 1133 containing the basic routines that help to transfer information between elements within computer system 1110, such as during start-up, may be stored in ROM 1131. RAM 1132 may contain data and/or program modules that are immediately accessible to and/or presently being operated on by the processors 1120. System memory 1130 may additionally include, for example, operating system 1134, application programs 1135, other program modules 1136 and program data 1137.

The computer system 1110 also includes a disk controller 1140 coupled to the bus 1105 to control one or more storage devices for storing information and instructions, such as a hard disk 1141 and a removable media drive 1142 (e.g., floppy disk drive, compact disc drive, tape drive, and/or solid state drive). The storage devices may be added to the computer system 1110 using an appropriate device interface (e.g., a small computer system interface (SCSI), integrated device electronics (IDE), Universal Serial Bus (USB), or FireWire).

The computer system 1110 may also include a display controller 1165 coupled to the bus 1105 to control a display 1166, such as a cathode ray tube (CRT) or liquid crystal display (LCD), for displaying information to a computer user. The computer system 1110 includes an input interface 1160 and one or more input devices, such as a keyboard 1162 and a pointing device 1161, for interacting with a computer user and providing information to the processor 1120. The pointing device 1161, for example, may be a mouse, a trackball, or a pointing stick for communicating direction information and command selections to the processor 1120 and for controlling cursor movement on the display 1166. The display 1166 may provide a touch screen interface which allows input to supplement or replace the communication of direction information and command selections by the pointing device 1161.

The computer system 1110 may perform a portion or all of the processing steps of embodiments of the invention in response to the processors 1120 executing one or more sequences of one or more instructions contained in a memory, such as the system memory 1130. Such instructions may be read into the system memory 1130 from another computer readable medium, such as a hard disk 1141 or a removable media drive 1142. The hard disk 1141 may contain one or more datastores and data files used by embodiments of the present invention. Datastore contents and data files may be encrypted to improve security. The processors 1120 may also be employed in a multi-processing arrangement to execute the one or more sequences of instructions contained in system memory 1130. In alternative embodiments, hard-wired circuitry may be used in place of or in combination with software instructions. Thus, embodiments are not limited to any specific combination of hardware circuitry and software.

As stated above, the computer system 1110 may include at least one computer readable medium or memory for holding instructions programmed according to embodiments of the invention and for containing data structures, tables, records, or other data described herein. The term "computer readable medium" as used herein refers to any medium that participates in providing instructions to the processor 1120 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1141 or removable media drive 1142. Non-limiting examples of volatile media include dynamic memory, such as system memory 1130. Non-limiting examples of transmission media include coaxial cables, copper wire, and fiber optics, including the wires that make up the bus 1105. Transmission media may also take the form of acoustic or light waves, such as those generated during radio wave and infrared data communications.

The computing environment 1100 may further include the computer system 1110 operating in a networked environment using logical connections to one or more remote computers, such as remote computer 1180. Remote computer 1180 may be a personal computer (laptop or desktop), a mobile device, a server, a router, a network PC, a peer device or other common network node, and typically includes many or all of the elements described above relative to computer system 1110. When used in a networking environment, computer system 1110 may include modem 1172 for establishing communications over a network 1171, such as the Internet. Modem 1172 may be connected to bus 1105 via user network interface 1170, or via another appropriate mechanism.

Network 1171 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1110 and other computers (e.g., remote computer 1180). The network 1171 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1171.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A computer-implemented method for performing a cardiovascular T1-weighted turbo-spin-echo magnetic resonance imaging sequence at high heart rates greater than 80 bpm, comprising:
   receiving a physiological signal from a subject, the physiological signal representative of the subject's heartbeat;
   performing dark-blood preparation according to a trigger pulse of N, wherein the dark-blood preparation occurs only in every Nth heartbeat and N is greater than 1, wherein the dark-blood preparation comprises:
   performing a spatially nonselective inversion pulse, and
   performing a slice selective inversion pulse of an imaging slice,
   such that blood magnetization outside the imaging slice is inverted;
   performing a first data readout in every Nth heartbeat, wherein the first data readout includes capturing first imaging data associated with the imaging slice when the subject's heart is in diastole and the blood from outside the imaging slice has moved into the imaging slice and blood magnetization is zero, wherein the performance of the first data readout has a magnetic saturation effect on the imaging slice;

performing maintenance pulses, wherein each of the maintenance pulses are performed only for every heartbeat that does not include a data readout, wherein the performance of each of the maintenance pulses has the magnetic saturation effect on the imaging slice such that performing the first data readout in every Nth heartbeat and performing each of the maintenance pulses for every heartbeat that does not include a data readout provides for steady state maximum T1-weighting of the imaging slice, wherein each of the maintenance pulses is a slice selective saturation pulse that saturates transverse and longitudinal magnetization of the imaging slice and does not include a data readout; and reconstructing a T1-weighted image of the imaging slice based on the first imaging data received as a result of the first data readouts.

2. The computer-implemented method of claim 1, wherein the physiological signal is an electrocardiogram wave.

3. The computer-implemented method of claim 2, wherein the dark-blood preparation is triggered by an R-wave preceding every Nth heartbeat.

4. The computer-implemented method of claim 1, wherein the physiological signal is a pulse oximetry wave.

5. The computer-implemented method of claim 1, further comprising: determining the trigger pulse of N based on a parameter representative of the subject's heart rate.

6. The computer-implemented method of claim 5, wherein the parameter representative of the subject's heart rate is an average value for the heart rate.

7. The computer-implemented method of claim 5, wherein determining the trigger pulse value of N includes comparing the parameter representative of the subject's heart rate to one or more threshold values or using a lookup table.

8. A computer-implemented method for producing a cardiovascular T1-weighted magnetic resonance image at high heart rates greater than 80 bpm, comprising:

receiving a parameter representative of a subject's heart rate;

determining a trigger pulse value N for an MRI sequence based on the parameter representative of the subject's heart rate;

performing the MRI sequence, including:
performing dark-blood preparation according to a trigger pulse of N, wherein the dark-blood preparation occurs only in every Nth heartbeat, wherein the dark blood preparation comprises:
performing a spatially nonselective inversion pulse, and
performing a slice selective inversion pulse of an imaging slice,
such that a blood magnetization outside the imaging slice is inverted; and
performing one of a first data readout or a maintenance pulse for every heartbeat, wherein the first data readout includes capturing imaging data associated with an imaging slice when the subject's heart is in diastole and the blood from outside the imaging slice has moved into the imaging slice and blood magnetization is zero, and both the first data readout and the maintenance pulse saturate transverse and longitudinal magnetization of the imaging slice such that both the first data readout and the maintenance pulse have a magnetic saturation effect on the imaging slice, wherein the performing one of the first data readout or the maintenance pulse for every heartbeat provides for a steady state of maximum T1-weighting of the imaging slice; and
reconstructing a T1-weighted image of the imaging slice based on the imaging data received as a result of the first data readouts.

9. The computer-implemented method of claim 8, wherein the parameter representative of the subject's heart rate is a physiological signal.

10. The computer-implemented method of claim 8, wherein the parameter representative of the subject's heart rate is an average value for the heart rate.

11. The computer-implemented method of claim 8, wherein determining the trigger pulse value N includes comparing the parameter representative of the subject's heart rate to one or more threshold values or using a lookup table.

12. The computer-implemented method of claim 8, wherein the first data readout and the maintenance pulse occur while the subject's heart is in diastole.

13. The computer-implemented method of claim 8, wherein the maintenance pulse includes a second data readout that produces a second data set which is not used in the image reconstruction.

* * * * *